US012625138B2

(12) United States Patent
Kuo et al.

(10) Patent No.: US 12,625,138 B2
(45) Date of Patent: May 12, 2026

(54) ANTIBODY FOR PORCINE REPRODUCTIVE AND RESPIRATORY SYNDROME VIRUS AND USES THEREOF

(71) Applicant: NOVASCOPE BIOCHIPS INC., Dover, DE (US)

(72) Inventors: Chang-Fu Kuo, Taipei (TW); Ming-Tang Chiou, Taipei (TW); Wei-Hao Lin, Taipei (TW); Lian-Chin Wang, Taipei (TW); Ao-Ho Hsieh, Taipei (TW)

(73) Assignee: NOVASCOPE BIOCHIPS INC.

( * ) Notice: Subject to any disclaimer, the term of this patent is extended or adjusted under 35 U.S.C. 154(b) by 588 days.

(21) Appl. No.: 18/184,907

(22) Filed: Mar. 16, 2023

(65) Prior Publication Data

US 2023/0324388 A1     Oct. 12, 2023

Related U.S. Application Data

(60) Provisional application No. 63/321,209, filed on Mar. 18, 2022.

(51) Int. Cl.
| | |
|---|---|
| *G01N 33/569* | (2006.01) |
| *C07K 1/04* | (2006.01) |
| *C07K 16/10* | (2026.01) |
| *C07K 16/108* | (2026.01) |
| *C12N 15/63* | (2006.01) |
| *G01N 27/414* | (2006.01) |
| *G01N 33/543* | (2006.01) |

(52) U.S. Cl.
CPC ....... *G01N 33/56983* (2013.01); *C07K 1/042* (2013.01); *C07K 16/10* (2013.01); *C07K 16/108* (2026.01); *C12N 15/63* (2013.01);

*G01N 27/4145* (2013.01); *G01N 33/54373* (2013.01); *C07K 2317/33* (2013.01); *C07K 2317/565* (2013.01); *G01N 2333/08* (2013.01); *G01N 2469/10* (2013.01)

(58) Field of Classification Search
None
See application file for complete search history.

(56) References Cited

U.S. PATENT DOCUMENTS

| | | |
|---|---|---|
| 2003/0017448 A1 | 1/2003 | Osorio |
| 2007/0009526 A1 | 1/2007 | Benson et al. |
| 2011/0123541 A1 | 5/2011 | Bachmann et al. |
| 2012/0034229 A1 | 2/2012 | Rousselle et al. |
| 2019/0257829 A1 | 8/2019 | Ludwig et al. |
| 2019/0336615 A1 | 11/2019 | Thompson et al. |
| 2020/0407462 A1 | 12/2020 | Bamdad |

OTHER PUBLICATIONS

Shao et al., Near-infrared electrochemiluminesence biosensor for high sensitive detection of porcine reproductive and respiratory syndrome virus based on cyclodextrin-grafted porous Au/PtAu nanotube Sensor. Actuat. B Chem. 2017; vol. 240, pp. 586-594.
International Search Report, Written Opinion and Notification of Transmittal mailed Aug. 29, 2023 in International Application PCT/US2023/064546.

*Primary Examiner* — Thomas J. Visone
*Assistant Examiner* — Danyal Hassan Alam
(74) *Attorney, Agent, or Firm* — ScienBiziP, P.C.

(57) ABSTRACT

The instant disclosure discloses an antibody or antigen-binding fragment thereof binding to Porcine Reproductive and Respiratory Syndrome Virus (PRRSV), and uses of such antibody or antigen-binding fragment thereof to create immunoassay methods or devices for PRRSV detection.

20 Claims, 2 Drawing Sheets

Specification includes a Sequence Listing.

1

ANTIBODY FOR PORCINE REPRODUCTIVE AND RESPIRATORY SYNDROME VIRUS AND USES THEREOF

CROSS-REFERENCE TO RELATED APPLICATION

This application claims benefit of and priority to U.S. Provisional Patent Application Ser. No. 63/321,209, entitled "ANTIBODY FOR PORCINE REPRODUCTIVE AND RESPIRATORY SYNDROME VIRUS (PRRSV)", filed on Mar. 18, 2022. The contents of the above-mentioned application are hereby incorporated by reference herein for all purposes.

REFERENCE TO SEQUENCE LISTING

Accompanying this application is a sequence listing in an XML file named "2022A-149447-SequenceListing.xml", created Mar. 16, 2023, and having a size of 13,755 bytes. The sequence listing is hereby fully incorporated by reference herein.

FIELD

The present disclosure generally relates to an antibody or an antigen-binding fragment and, more specifically, relates to an antibody or an antigen-binding fragment for recognizing Porcine Reproductive and Respiratory Syndrome Virus and use of the same.

BACKGROUND

Porcine reproductive and respiratory syndrome (PRRS) is viewed by many as the most important disease currently affecting the pig industry worldwide. Porcine reproductive and respiratory syndrome causes severe reproduction losses, is associated with increased mortality due to secondary infections, and is linked to reduced feed conversion and average daily weight gain. Unfortunately, control of the virus that causes PRRS has proven to be difficult.

PRRSV is an enveloped single-stranded RNA virus classified in the family Arteriviridae (Cavanaugh, 1997). The virus causes a widespread disease of swine that was first described as a 'mystery swine disease' in the USA in 1987 (Hill, 1990). The disease manifests as respiratory illness in all age groups of swine leading to death in some younger pigs and severe reproductive problems in breeding-age females.

PRRSV infection is widespread on most pig farms in the world. PRRSV has been found to cause low survival rates and low feed conversion rates (FCRs) of infected pigs and results in great economic losses in pig farming. There are some PRRSV test kits for commercial use. However, the PRRSV test kits that are commercially available typically involve long testing times and involve a need to prepare more reagents. Therefore, it is important to develop PRRSV test kits that can detect PRRSV more easily and quickly.

SUMMARY

The present disclosure is directed to an antibody or an antigen-binding fragment and, more specifically, to an antibody or an antigen-binding fragment for recognizing Porcine Reproductive and Respiratory Syndrome Virus and use of the same.

According to a first aspect of the present disclosure, an antibody or antigen-binding fragment thereof binding to PRRSV is provided, which includes: a heavy chain variable domain including a heavy chain complementarity-determining region 1 (CDR-H1) containing a sequence of SEQ ID NO: 1, a CDR-H2 containing a sequence of SEQ ID NO: 2, and a CDR-H3 containing a sequence of SEQ ID NO: 3; and a light chain variable domain including a light chain complementarity-determining region 1 (CDR-L1) containing a sequence of SEQ ID NO: 4, a CDR-L2 containing a sequence of Ala-Ala-Ser, and a CDR-L3 containing a sequence of SEQ ID NO: 5.

In an implementation of the first aspect of the present disclosure, the heavy chain variable domain further includes a sequence of SEQ ID NO: 6.

In another implementation of the first aspect of the present disclosure, the light chain variable domain further includes a sequence of SEQ ID NO: 7.

According to a second aspect of the present disclosure, an isolated nucleic acid encoding the antibody or antigen-binding fragment thereof of the first aspect of the present disclosure is provided, the isolated nucleic acid encoding the antibody or antigen-binding fragment thereof comprises a first fragment encoding a heavy chain variable domain and a second fragment encoding a light chain variable domain.

In an implementation of the second aspect of the present disclosure, the first fragment encoding the heavy chain variable domain further includes a sequence of SEQ ID NO: 8.

In an implementation of the first aspect of the present disclosure, the second fragment encoding the light chain variable domain further includes a sequence of SEQ ID NO: 9.

According to a third aspect of the present disclosure, a vector including the isolated nucleic acid of the second aspect of the present disclosure is provided.

According to a fourth aspect of the present disclosure, a host cell including the vector of the third aspect of the present disclosure is provided.

According to a fifth aspect of the present disclosure, a method for producing an antibody or antigen-binding fragment thereof binding to PRRSV is provided, which includes: (a) culturing the host cell of the fourth aspect of the present disclosure under conditions suitable for expressing the antibody or antigen-binding fragment thereof; and (b) recovering the antibody or antigen-binding fragment thereof.

In an implementation of the fifth aspect of the present disclosure, the heavy chain variable domain further includes a sequence of SEQ ID NO: 6.

In another implementation of the fifth aspect of the present disclosure, the light chain variable domain further includes a sequence of SEQ ID NO: 7.

According to a sixth aspect of the present disclosure, a method for detecting PRRSV is provided, and the method includes contacting a sample with the antibody or antigen-binding fragment thereof of the first aspect of the present disclosure.

In another implementation of the sixth aspect of the present disclosure, the heavy chain variable domain further includes a sequence of SEQ ID NO: 6.

In another implementation of the sixth aspect of the present disclosure, the light chain variable domain further includes a sequence of SEQ ID NO: 7.

According to a seventh aspect of the present disclosure, a biological field-effect transistor (Bio-FET) is provided, which includes: a transistor region; and a detecting region, wherein the detecting region includes a detecting surface that is functionalized with an antibody or antigen-binding fragment thereof binding to PRRSV wherein the antibody or antigen-binding fragment thereof includes: a heavy chain variable domain including a heavy chain complementarity-determining region 1 (CDR-H1) containing a sequence of SEQ ID NO: 1, a CDR-H2 containing a sequence of SEQ ID NO: 2, and a CDR-H3 containing a sequence of SEQ ID NO: 3; and a light chain variable domain including a light chain complementarity-determining region 1 (CDR-L1) containing a sequence of SEQ ID NO: 4, a CDR-L2 containing a sequence of Ala-Ala-Ser, and a CDR-L3 containing a sequence of SEQ ID NO: 5.

In another implementation of the seventh aspect of the present disclosure, the heavy chain variable domain further includes a sequence of SEQ ID NO: 6.

In another implementation of the seventh aspect of the present disclosure, the light chain variable domain further includes a sequence of SEQ ID NO: 7.

According to an eighth aspect of the present disclosure, a method for detecting PRRSV by using a biological field-effect transistor (Bio-FET) is provided, and the method includes: (a) contacting a sample with an antibody or antigen-binding fragment thereof immobilized on a detecting surface of the Bio-FET, wherein the antibody or antigen-binding fragment thereof includes: a heavy chain variable domain including a heavy chain complementarity-determining region 1 (CDR-H1) containing a sequence of SEQ ID NO: 1, a CDR-H2 containing a sequence of SEQ ID NO: 2, and a CDR-H3 containing a sequence of SEQ ID NO: 3; and a light chain variable domain including a CDR-L1 containing a sequence of SEQ ID NO: 4, a CDR-L2 containing a sequence of Ala-Ala-Ser, and a CDR-L3 containing a sequence of SEQ ID NO: 5, wherein the antibody or antigen-binding fragment thereof binds to PRRSV; and (b) analyzing an electric signal obtained from the Bio-FET.

In another implementation of the eighth aspect of the present disclosure, the heavy chain variable domain further includes a sequence of SEQ ID NO: 6.

In another implementation of the eighth aspect of the present disclosure, the light chain variable domain further includes a sequence of SEQ ID NO:7.

With application to the aforementioned antibody or antigen-binding fragment thereof, the antibody or antigen-binding fragment thereof specifically recognizes PRRSV with high sensitivity, leading to excellent detection of PRRSV, thereby being applied to various uses, for example, western blotting, chemiluminescence microparticle immunoassay (CMIA), chemiluminescence immunoassay (CLIA), lateral flow immunoassay (LFIA) or Enzyme-linked immunosorbent assay (ELISA), or using Biochip devices (e.g., Bio-FET).

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1A:
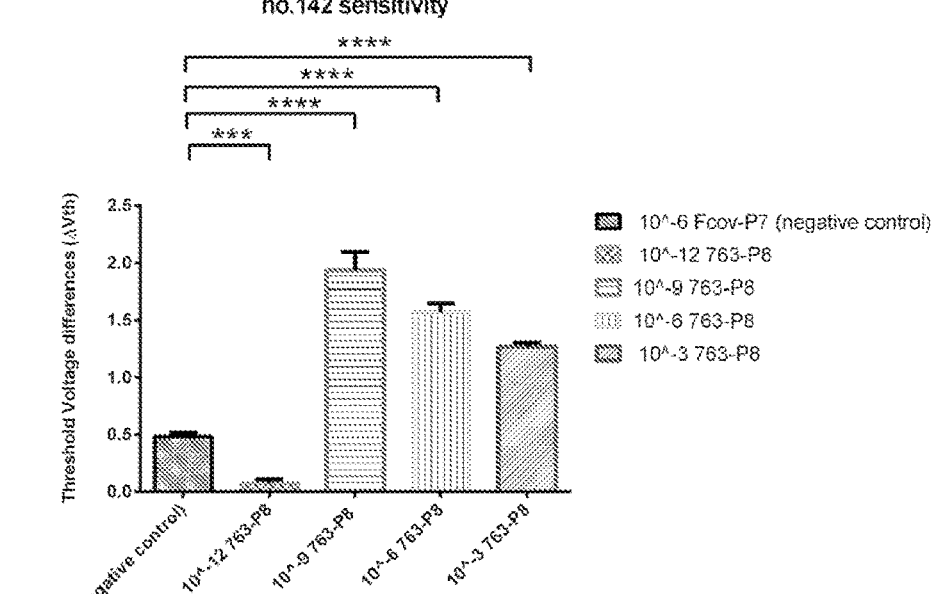
FIG. 1A illustrates the sensitivity of anti-PRRSV antibody 142 (denoted as no. 142) to PRRSV (denoted as 763-P8) or coronavirus (denoted as FCOV-P7) when being applied on Bio-FET.

The detailed description provided below in connection with the appended drawings is intended as a description of the present examples and is not intended to represent the only forms in which the present examples may be constructed or utilized. The description sets forth the functions of the examples and the sequence of steps for constructing and operating the examples. However, the same or equivalent functions and sequences may be accomplished by different examples.

Definitions

For convenience, certain terms employed in the specification, examples, and appended claims are collected here. Unless otherwise defined herein, scientific, and technical terminologies employed in the present disclosure shall have the meanings that are commonly understood and used by one of ordinary skill in the art. Also, unless otherwise required by context, it will be understood that singular terms shall include plural forms of the same, and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

The terms "first", "second", and "third" in the description of the present invention and the above-mentioned drawings are used to distinguish different objects, rather than to describe a specific order.

The term "antibody" is used in the broadest sense and specifically covers monoclonal antibodies (including full-length monoclonal antibodies), polyclonal antibodies, multi-specific antibodies (e.g., bi-specific antibodies), and antibody fragments so long as they exhibit the desired biological activity. "Antibody fragments" include a portion of a full-length antibody, generally the antigen binding or variable region thereof. Examples of antibody fragments include Fab, Fab', F(ab')2, rIgG, and Fv fragments; diabodies; linear antibodies; single-chain antibody molecules; and multi-specific antibodies formed from antibody fragments.

"Antibody fragments" include only a portion of an intact antibody, wherein the portion retains at least one, and as many as most or all, of the functions normally associated with that portion when present in an intact antibody. In one embodiment, an antibody fragment includes an antigen-binding site of the intact antibody and thus retains the ability to bind the antigen. In another embodiment, an antibody fragment, for example, one that includes the Fc region, retains at least one of the biological functions normally associated with the Fc region when present in an intact antibody, antibody half-life modulation, antibody-dependent cell-mediated cytotoxicity (ADCC) function, and complement binding. In one embodiment, an antibody fragment is a monovalent antibody that has an in vivo half-life substantially similar to that of an intact antibody. For example, such an antibody fragment may include an antigen-binding arm linked to an Fc sequence capable of conferring in vivo stability to the fragment. The antibody fragment in the present disclosure may exist in a variety of forms including, for example, variable fragment (Fv), single-chain variable fragment (scFv), antigen-binding fragment (Fab), reduced IgG (rIgG), and divalent antibody fragment [F(ab')2], as well as single-chain antibodies.

The "variable region" or "variable domain" of an antibody refers to the amino-terminal domains of the heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies but is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each include four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as the participation of the antibody in antibody-dependent cellular toxicity.

The term "complementarity-determining region" (CDR) used herein refers to the hypervariable region of an antibody molecule that forms a surface complementary to the 3-dimensional surface of a bound antigen. Proceeding from N-terminus to C-terminus, each of the antibody heavy and light chains includes three CDRs (CDR1, CDR2, and CDR3). Therefore, the antibody includes a total of six CDRs that include three CDRs from the variable region of a heavy chain and three CDRs from the variable region of a light chain.

As discussed herein, minor variations in the amino acid sequences of antibodies are contemplated as being encompassed by the presently disclosed and claimed inventive concept(s), providing that the variations in the amino acid sequence maintain at least 85% sequence identity. Antibodies of the present disclosure may be modified specifically to alter a feature of the peptide unrelated to its physiological activity. For example, certain amino acids can be changed and/or deleted without affecting the physiological activity of the antibody in this study (e.g., its ability to detect PRRSV). In particular, conservative amino acid replacements are contemplated. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of antibodies can be readily prepared by those of ordinary skill in the art. Preferred amino- and carboxyl-termini of fragments or analogs occur near boundaries of functional domains.

Anti-PRRSV antibody 142 is denoted as antibody 142, no. 142, or 142; anti-PRRSV antibody 277 is denoted as antibody 277, no. 277, or 277.

(i) Antibody Preparation

According to certain embodiments of the present disclosure, the antibody is derived from a hybridoma clone 142, designated as antibody 142. In these embodiments, the CDR-H1, CDR-H2, CDR-H3, CDR-L1, CDR-L2, CDR-L3, CDR-VH (heavy chain variable domain), and CDR-VL (light chain variable domain) of antibody 142 includes the amino acid sequences shown in the sequence listing.

The anti-PRRSV antibody of the present disclosure may be produced by a production method as described below. Specifically, for example, nonhuman mammals such as antibody-producing mice are immunized with PRRSV, a part of PRRSV, or a conjugate of the part of PRRSV and an appropriate carrier substance (e.g., bovine serum albumin) for enhancing antigenicity together with, if necessary, an immuno-augmenting agent (e.g., Freund's complete or incomplete adjuvant). As PRRSV, both natural PRRSV and recombinant PRRSV may be used. Alternatively, immunization may be performed by introducing a gene encoding PRRSV and then administering animal cells that overexpress PRRSV on their cell surfaces. A monoclonal antibody may be obtained by fusing antibody-producing cells obtained from immunized animals to myeloma cells incapable of producing any autoantibody, culturing the thus-obtained hybridomas, and then selecting clones that produce the monoclonal antibody showing a specific affinity for an antigen used for immunization.

Alternatively, to certain embodiments of the present disclosure, the present antibody (e.g., antibody 142) may be produced by DNA cloning. DNA encoding the present antibody may be easily isolated and sequenced by use of conventional procedures, such as using oligonucleotide probes that are capable of binding specifically to genes encoding the heavy and light chains of the antibody. The DNA sequences encoding the CDR-H1, CDR-H2, CDR-H3, CDR-L1, CDR-L2, and CDR-L3 of the antibody 142 used herein are also shown in the sequence listing provided below. Once isolated, the DNA may be placed into expression vectors which are then transfected into host cells and cultured under conditions suitable for expression. The term "expression vector" refers to a nucleic acid molecule capable of transporting another nucleic acid to which it has been linked. In one embodiment, the vector used herein is an expression vector and maybe a "plasmid", which refers to a circular double-stranded DNA loop into which additional DNA segments may be ligated. In another embodiment, the vector used herein is an expression vector and may be a viral vector, wherein an additional DNA segment can be ligated into the viral genome for expressing the antibodies. The vectors disclosed herein are capable of self-replicating in a host cell into which they have been introduced (for example, a bacterial vector having a bacterial replication origin and an episomal mammalian vector) or may be integrated into the genome of a host cell upon introduction into the host cell, thereby being replicated along with the host genome (e.g., a non-episomal mammalian vector). The host cells may be E. coli cells, yeast cells, insect cells, HEK293 cells, simian COS cells, or Chinese hamster ovary (CHO) cells, or myeloma cells that do not produce immunoglobulin proteins, to synthesize the desired antibodies in the recombinant host cells.

All degenerate nucleotide sequences are included within the scope of the disclosure as long as the peptide/polypeptide/protein (e.g., the present CDR, VH region, or VL region) encoded by the nucleotide sequence maintains the desired activity or function. The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

Depending on intended uses, the present antibody or the DNA encoding the antibody may be used to produce chimeric antibodies (e.g., bi-specific antibodies), and/or antibody fragments derived thereof.

(ii) Method for Detecting Porcine Reproductive and Respiratory Syndrome Virus (PRRSV)

According to certain embodiments, the method for detecting PRRSV includes the steps of: (a) preparing a sample; (b) contacting the sample with the present antibody or antigen-binding fragment thereof, and (c) determining the signal from the detection. The sample may be first lysed by a method familiar to a person skilled in the art, for example, freezing and thawing, sonication, pressure, enzyme, detergent, or a combination thereof. The virus in the samples is then detected by the present method or antibody via suitable assay, for instance, western blotting, chemiluminescence microparticle immunoassay (CMIA), chemiluminescence immunoassay (CLIA), lateral flow immunoassay (LFIA), or enzyme-linked immunosorbent assay (ELISA), or using biochip devices (e.g., Bio-FET).

The following Examples are provided to elucidate certain aspects of the present disclosure and to aid those of skill in the art in practicing this disclosure. These Examples are in no way to be considered to limit the scope of the disclosure in any manner. Without further elaboration, it is believed that one skilled in the art can, based on the description herein, utilize the present disclosure to its fullest extent. All publications cited herein are hereby incorporated by reference in their entirety.

EXAMPLES

Example 1

Preparation of the Anti-PRRSV Antibodies
1.1 Antigen Preparation

The viral lysate of PRRSV, porcine pseudorabies virus (denoted as S1462), porcine coronavirus (denoted as NTU), and porcine circovirus type 2 (denoted as 110-873 S) are from Dr. Chiou Ming-Tang of National Pingtung University of Science and Technology (NPUST). The unit concentration of viral lysate is determined by Bradford protein assay (BIO-RAD, USA) and diluted by 0.22 micron filtered phosphate-buffered saline (PBS) buffer. The viral lysate is aliquoted and stored at −80° C. ready for use.
1.2 Immunization In order to generate anti-PRRSV antibodies, 6-8 weeks-old female BALB/c mice received an intraperitoneal injection with 100 µg (1 µg/µL) PRRSV viral lysate emulsified with the same volume of complete Freund's adjuvant (Sigma-Aldrich, USA) respectively.

Boosting is performed with 100 µg PRRSV viral lysate in incomplete Freund's adjuvant (Sigma-Aldrich, USA) on days 14, 28, and 42. Before sacrifice, the antibody response is provoked by injection with 50 µg PRRSV viral lysate emulsified with incomplete Freund's adjuvant twice at three-day intervals before sacrifice.
1.3 Hybridoma Preparation and Antibody Purification At the end of the immunization schedule, mice spleens are collected immediately and fused with myeloma cells for hybridoma preparation and semi-solid selection subsequently (ClonaCell Hybridoma kit, STEMCELL Technologies, USA). All protocol is followed to the manufacturers' instructions. Hybridoma colonies are propagated in 96-well microtiter plates (Product No. 3788, Corning, USA) until cells at confluency and their supernatants are harvested to examine antibody response to PRRSV by ELISA test (PRRS X3 Ab Test, IDEXX, USA; described below). Antibodies 142 and 277 with high binding affinity to PRRSV are selected and purified by protein G Sepharose resin (Cytiva, USA). These purified monoclonal antibodies are dialyzed with PBS buffer to remove glycine and concentrated with Amicon Ultra-15 centrifugal filter units (10 kDa, Merck Millipore, USA). Monoclonal antibodies are stored at −80° C. for the following experiment.
1.4 Determining the Binding Affinity of Anti-PRRSV Antibodies In order to determine the binding affinity of the instant anti-PRRSV antibodies to PRRSV, an ELISA is performed. First, 96-well microtiter plates are coated with 100 ng of PRRSV viral lysate, which is from Dr. Chiou Ming-Tang of National Pingtung University of Science and Technology (NPUST). Then, 0.5 µg of anti-PRRSV antibody 142 or 277 is added as a primary antibody in each well for reacting for 1 hour at room temperature (RT). After 1 hour reaction, unbound antibodies are removed by washing buffer (Tris-buffered saline (TBS) with 0.05% Tween 20). Then, 4000× diluted anti-Mouse IgG-HRP (Jackson ImmunoResearch Laboratory, Code: 515-005-071, USA) is added as a secondary antibody for reacting for 2 hours at RT. After washing with washing buffer (Tris-buffered saline (TBS) with 0.05% Tween 20), the optical density (OD) value is evaluated by measuring the absorbance at 450 nm wavelength (EZ Read 400 Microplate Reader, Biochrom, USA). In the results (not shown), anti-PRRSV antibodies 142 and 277 have higher OD450 values, indicating that antibodies 142 and 277 have high binding affinity to PRRSV, so these two antibodies are selected. Moreover, the anti-PRRSV antibody 277 is used as a comparative example in further examples.
1.5 Characterization of Two Clones of Anti-PRRSV Antibodies According to certain embodiments of the present disclosure, gene sequences of antibody variable regions are resolved from mRNA extracts of anti-PRRSV antibody 142. The gene sequences are then analyzed by IgBlast [IgBlast tool provided by the National Institutes of Health (NIH) (nih.gov)]. After the CDR information is obtained, the polynucleotide sequence (denoted as a DNA sequence) is translated into a polypeptide sequence (denoted as an amino acid sequence) by ExPASy Translate (a tool for translating a nucleotide sequence to a protein sequence, provided by the Swiss Institute of Bioinformatics (SIB)). The polynucleotide sequence (denoted as a DNA sequence) of the 142 VH domain (SEQ ID NO: 8) is translated into the polypeptide sequence (denoted as an amino acid sequence) as the SEQ ID NO: 6, and three CDR sequences of which are the SEQ ID NO: 1 (CDR-H1), SEQ ID NO: 2 (CDR-H2), and SEQ ID NO: 3 (CDR-H3). The polynucleotide sequence (denoted as a DNA sequence) of the 142 VL domain (SEQ ID NO: 9) is translated into the polypeptide sequence (denoted as an amino acid sequence) as the SEQ ID NO: 7, and three CDR sequences of which are the SEQ ID NO: 4 (CDR-L1), SEQ ID NO: 5 (CDR-L3) and CDR-L2 containing a sequence of Ala-Ala-Ser.

Example 2

The Limit of Quantification for the Anti-PRRSV Antibody

In order to determine the smallest amount or the lowest concentration of PRRSV that is possible to be quantified with suitable accuracy and precision by the instant anti-PRRSV antibodies 142 and 277, the limit of quantification is confirmed as follows.

The lowest concentration of PRRSV which can be recognized by the anti-PRRSV antibodies 142 and 277 through an ELISA test is examined. First, the 96-well microtiter plates are coated with 0.78-100 ng of PRRSV viral lysate. Then, 1 µg of the indicated anti-PRRSV antibody is added as a primary antibody in each well for reacting for 1 hour at RT. After removing unbound antibodies by using washing buffer, 2500× diluted anti-Mouse IgG-HRP is added as a secondary antibody in each well for reacting for 2 hours at RT. After washing with washing buffer, TMB is added and incubated at RT for 30 mins. The OD value at 450 nm is evaluated by an EZ Read 400 Microplate Reader.

The result for determination of limit of quantification of antibodies 142 and 277 against PRRSV is presented in Table 1. The value of OD 450 is shown in Table 1, and the background values herein are around 0.15-0.2. As shown in Table 1, the concentration of 142 is 1 µg; the concentration of 277 is 1 µg. Comparing the results for determination of limit of quantification of 142 and 277, both 142 and 277 have the ability to detect 0.78-100 ng of PRRSV viral lysate. The lowest concentration of PRRSV which can be recognized by both of the anti-PRRSV antibodies 142 and 277 through the ELISA test is at least 0.78 ng.

Table 1. Results for determination of limit of quantification of each clone of anti-PRRSV antibody against PRRSV by ELISA.

| PRRSV viral lysate (ng) | No. 142 1 µg | No. 277 1 µg |
|---|---|---|
| 100 | 1.576 | 1.816 |
| 50.00 | 1.357 | 1.683 |
| 25.00 | 1.305 | 1.558 |
| 12.50 | 1.106 | 1.538 |
| 6.25 | 1.164 | 1.555 |
| 3.13 | 0.959 | 1.453 |
| 1.56 | 1.046 | 1.528 |
| 0.78 | 0.984 | 1.457 |

Example 3

Cross-Reactivity of the Anti-PRRSV Antibody
Test 1

In order to confirm the specificity of the anti-PRRSV antibodies 142 and 277, the cross-reactivity of the antibodies 142 and 277 against PRRSV viral lysate and lysate of other viruses through an ELISA test is examined. First, 96-well microtiter plates are coated with PRRSV viral lysate (denoted as PRRSV) and lysate of pseudorabies virus (denoted as S1462) and porcine coronavirus (denoted as NTU). Then, 1:4000 diluted, purified anti-PRRSV antibodies 142 and 277

(with the original concentration of 0.8-1.0 mg/mL) are added as a primary antibody in each well for reacting for 2 hours at 4° C.

After removing unbound antibodies, 1:5000 diluted, Peroxidase AffiniPure Goat Anti-Mouse IgG, light chain specific (Code: 115-035-174) is added as a secondary antibody for reacting for 2 hours at 4° C. After washing with washing buffer, TMB is added and incubated. The OD450 values are recorded using an EZ Read 400 Microplate Reader. Each viral lysate is tested for two separated repeats which are marked as Group 1 and Group 2, respectively. The result of OD450 values in Test 1 is presented in Table 2 below.

Test 2

In order to determine the cross-reactivity of antibodies 142 and 277 against PRRSV viral lysate and lysate of other viruses, an ELISA is performed. First, 96-well microtiter plates are coated with PRRSV viral lysate (denoted as PRRSV), lysate of porcine circovirus type 2 (denoted as 110-873S), and porcine coronavirus (denoted as NTU). Then, 1:4000 diluted, purified anti-PRRSV antibodies 142 and 277 (with the original concentration of 0.8-1.0 mg/mL) are added as a primary antibody in each well for reacting for 2 hours at 4° C.

After removing unbound antibodies, 1:2000 diluted in PBS, Peroxidase AffiniPure Goat Anti-Mouse IgG, light chain specific (Code: 115-035-174) is added as a secondary antibody for reacting for 2 hours at 4° C. After washing with washing buffer, TMB is added and incubated. The OD value at 450 nm is recorded using an EZ Read 400 Microplate Reader. The result of OD450 values in Test 2 is presented in Table 3 below.

Table 2. Result for determination of cross-reactivity of antibodies 142 and 277 against PRRSV viral lysate, lysate of pseudorabies virus (denoted as S1462), and porcine coronavirus (denoted as NTU) by ELISA.

| Viral lysate | No. 142 2' Ab 1: 2000 in PBS | | No. 277 2' Ab 1: 2000 in PBS | | PBS 2' Ab 1: 2000 in PBS | |
|---|---|---|---|---|---|---|
| Group | 1 | 2 | 1 | 2 | 1 | 2 |
| PRRSV | 0.385 | 0.344 | 0.154 | 0.091 | 0.073 | 0.058 |
| | | | | | 0.072 | 0.060 |
| S1462 | 0.082 | 0.080 | 0.063 | 0.088 | 0.080 | 0.054 |
| | | | | | 0.089 | 0.052 |
| NTU | 0.148 | 0.133 | 0.076 | 0.072 | 0.083 | 0.058 |
| | | | | | 0.119 | 0.054 |

Table 3. Results for determination of cross-reactivity of antibodies 142 and 277 against PRRSV viral lysate and porcine coronavirus (denoted as NTU) by ELISA.

| Viral lysate | No. 142 2' Ab 1: 2000 in PBS | No. 277 2' Ab 1: 2000 in PBS | PBS 2' Ab 1: 2000 in PBS |
|---|---|---|---|
| PRRSV | 0.411 | 0.303 | 0.118 |
| | | | 0.121 |
| NTU | 0.136 | 0.185 | 0.140 |
| | | | 0.145 |

As shown in Table 2 and Table 3, both the antibodies 142 and 277 had the ability to bind PRRSV viral lysate. More specificity, when comparing the antibody 142 to the antibody 277, antibody 277 tended to have a better specificity to PRRSV.

Example 4

Detecting PRRSV by the Anti-PRRSV Antibody Immobilized on a Biosensor Field-Effect Transistor (Bio-FET).

A Bio-FET has a transistor region and a detecting region, in which the detecting region further includes a detecting surface. In the example of the present disclosure, the detecting surface may be functionalized with the antibody or antigen-binding fragment thereof binding to Porcine Reproductive and Respiratory Syndrome Virus (PRRSV). More specifically, in this example, the anti-PRRSV antibodies 142 and 277 are able to be applied on a Bio-FET for detecting PRRSV in a sample. The following examples determine the cross-reactivity (e.g., specificity) and sensitivity of the anti-PRRSV antibodies 142 and 277 by using Bio-FET.

The steps of coating the anti-PRRSV antibody 142 or 277 on the Bio-FET are shown as follows:

1. Antibody immobilization
   a. Preparing 50 μL of 100 ng/mL anti-PRRSV antibody 142 or 277 solutions in 10 mM Bis-tris propane (BTP) buffer.
   b. The surface of the Bio-FET is submerged in the 100 ng/ml anti-PRRSV antibody 142 or 277 solutions overnight at 4° C. under a condition of 90% relative humidity.
2. Blocking by BSA
   a. The Bio-FET is then rinsed with 10 mM BTP buffer three times.
   b. The Bio-FET is submerged in 1% Bovine serum albumin (BSA) prepared with pH7, 1×PBS buffer for 30 minutes at 37° C.
   c. The Bio-FET is rinsed with 10 mM BTP buffer three times, followed by two rinses of deionized (DI) water, and blown dry. Then the Bio-FET is ready for use.

The steps of assaying anti-PRRSV antibody 142 or 277 are shown as follows:
   a. First, 100 μL of 10 mM, pH 7 BTP buffer is loaded by a pipette into the polydimethylsiloxane (PDMS) well on the Bio-FET. Then, 10 minutes are given to settle the system before the drain current-gate voltage (ID-VG) response is measured. Moreover, only after three successive overlapping ID-VG curves are obtained is the system deemed stable, and the last ID-VG curve can be called the baseline for the next steps in biosensing.
   b. The BTP buffer from the well is removed.
   c. 100 μL of the sample is loaded into the well and allowed to hybridize. More specifically, the sample is coronavirus, pseudorabies virus, or PRRSV. Furthermore, the sample is starting with the lowest concentration to higher concentrations.
   d. After 10 minutes, the sample is removed, and the well is rinsed with 100 μL of wash buffer (10 mM BTP with 0.05% Tween-20) with a pipette five times.
   e. Next, the well is rinsed with 100 μL of 10 mM, pH 7 BTP buffer with a pipette five times to remove any unspecific binding.
   f. A fresh 100 μL of 10 mM, pH 7 BTP buffer is loaded into the well after rinsing.

After 10 minutes for the system to settle, the ID-VG response is measured.

4.1. The Sensitivity of the Anti-PRRSV Antibody 142 and 277 Immobilized on a Bio-FET The sensitivity of the antibodies 142 and 277 are tested using the PRRSV viral lysate (denoted as 763-P8) with different dilution ratios, including $10^{-3}$, $10^{-6}$, $10^{-9}$, and $10^{-12}$ dilution, as testing samples. Moreover, porcine coronavirus (denoted as FCOV-P7) or pseudorabies virus (denoted as S1462-P7-PRV) with $10^{-6}$ dilution is used as a negative control. When the antibody is able to detect the lower concentration, the antibody has the higher sensitivity. When the target biomolecule (i.e., PRRSV) is bonded to the immobilized antibodies 142 or 277, the electric signal of the Bio-FET (represented as threshold voltage differences in the examples) would increase, and thus, in general, the higher the electric signal increase, the more of the biomolecule that is bound.

The result of the sensitivity of antibody 142 to PRRSV (denoted as 763-P8) is shown in FIG. 1A. The sample is PRRSV (denoted as 763-P8) with different dilution ratios, including $10^{-3}$, $10^{-6}$, $10^{-9}$, and $10^{-12}$ dilution. Moreover, porcine coronavirus (denoted as FCOV-P7) with $10^{-6}$ dilution is used as a negative control. As shown in FIG. 1A, the electric signals (threshold voltage differences) of antibody 142 to PRRSV (denoted as 763-P8) with $10^{-3}$, $10^{-6}$, and $10^{-9}$ is significantly higher than the negative control. Furthermore, the electric signal of the antibody 142 to PRRSV (denoted as 763-P8) with $10^{-9}$ dilution is 3 times higher than the negative control, which is the porcine coronavirus (denoted as FCOV-P7) with $10^{-6}$ dilution.

Figure 1B:
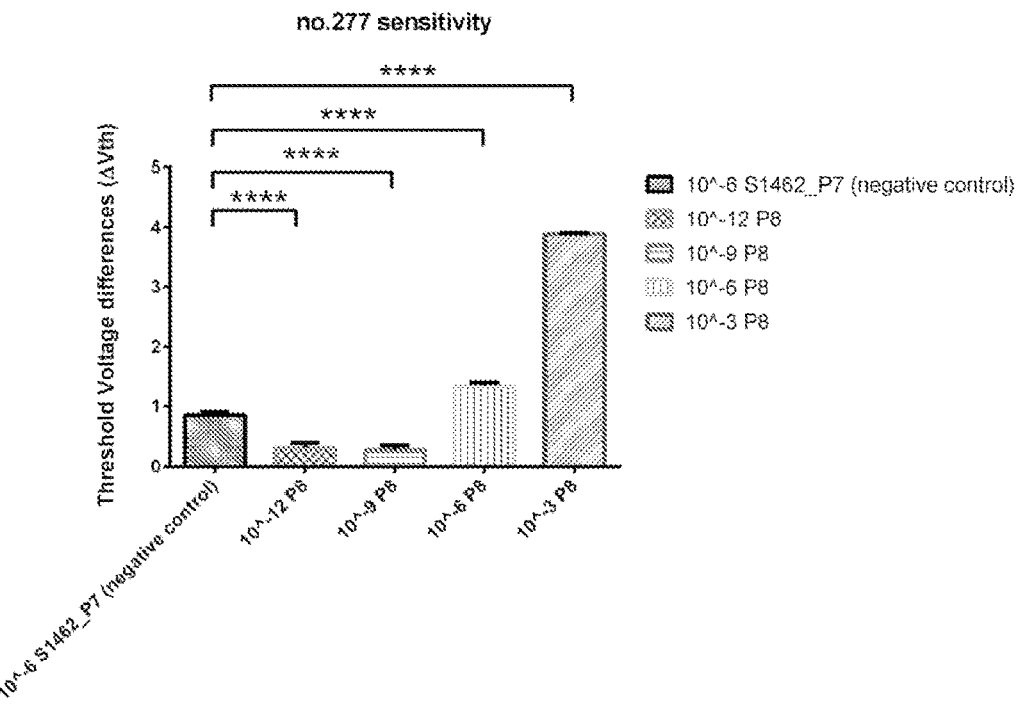
FIG. 1B illustrates the sensitivity of anti-PRRSV antibody 277 (denoted as no. 277) to PRRSV (denoted as 763-P8), or pseudorabies virus (denoted as S1462-P7-PRV) when being applied on Bio-FET.

The result of the sensitivity of the anti-PRRSV antibody 277 to PRRSV (denoted as 763-P8) is shown in FIG. 1B. The samples are PRRSV (denoted as 763-P8) with different dilution ratios, including $10^{-3}$, $10^{-6}$, $10^{-9}$, and $10^{-12}$ dilution. Moreover, pseudorabies virus (denoted as S1462-P7-PRV) with $10^{-6}$ dilution is used as a negative control. As shown in FIG. 1B, only the electric signals of the anti-PRRSV antibody 277 to PRRSV (denoted as 763-P8) with $10^{-3}$ and $10^{-6}$ dilution are significantly higher than the negative control, while the electric signals of the anti-PRRSV antibody 277 to PRRSV (denoted as 763-P8) with $10^{-9}$ and $10^{-12}$ dilution are even significantly lower than the negative control. Furthermore, only when the PRRSV with $10^{-3}$ dilution is used, the electric signal of the anti-PRRSV antibody 277 to PRRSV (denoted as 763-P8) could be 3 times higher than the negative control, which is the porcine coronavirus (denoted as FCOV-P7) with $10^{-6}$ dilution. Therefore, the results indicate that the sensitivity of the antibody 142 on the Bio-FET is better than that of the antibody 277.

4.2 the Cross-Reactivity of the Anti-PRRSV Antibodies 142 and 277 Immobilized on a Bio-FET In order to determine the specificity of the antibodies 142 and 277 immobilized on Bio-FET, the cross-reactivity of the antibodies 142 and 277 immobilized on Bio-FET against PRRSV (denoted as 763-P8) and other viruses, including pseudorabies virus (denoted as S1462-P7-PRV), porcine coronavirus (denoted as FCOV-P7), and porcine circovirus type 2 (denoted as 110-873S) are being determined by Bio-FET. When the antibodies show lower cross-reactivity, the antibodies have higher specificity.

Figure 2A:
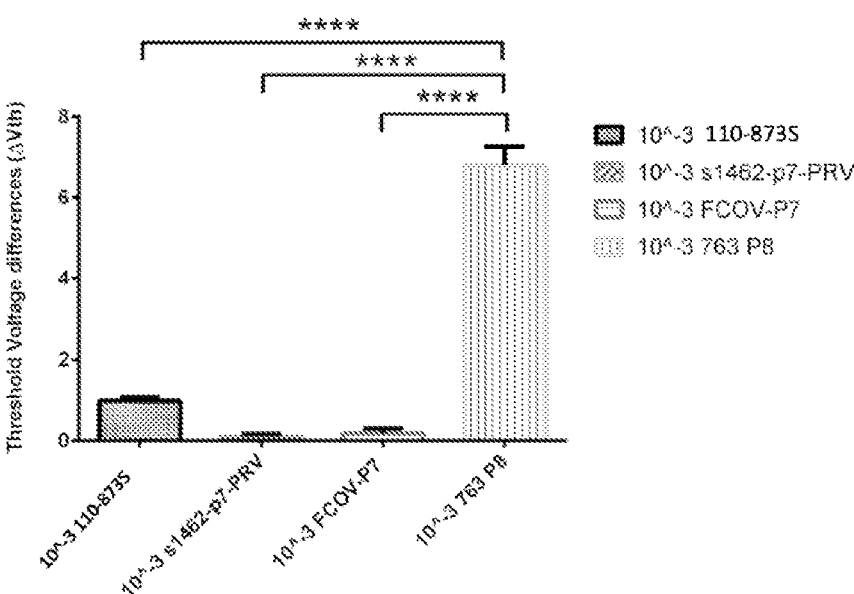
FIG. 2A illustrates the cross-reactivity of anti-PRRSV antibody 142 (denoted as no. 142) to PRRSV (denoted as 763-P8), pseudorabies virus (denoted as S1462-P7-PRV), coronavirus (denoted as FCOV-P7), or porcine circovirus type 2 (denoted as 110-873S) when being applied on Bio-FET.

The result of the cross-reactivity of anti-PRRSV antibody 142 to PRRSV (denoted as 763-P8), pseudorabies virus (denoted as S1462-P7-PRV), porcine coronavirus (denoted as FCOV-P7), and porcine circovirus type 2 (denoted as 110-873S) is shown in FIG. 2A. Those samples are used with $10^{-3}$ dilution. As shown in FIG. 2A, the electric signals of the anti-PRRSV antibody 142 to PRRSV (denoted as 763-P8) are significantly higher than the electric signals to pseudorabies virus (denoted as S1462-P7-PRV), porcine coronavirus (denoted as FCOV-P7), and porcine circovirus type 2 (denoted as 110-873S) with $10^{-3}$ dilution. Furthermore, the electric signal of the anti-PRRSV antibody 142 to PRRSV (denoted as 763-P8) with $10^{-3}$ dilution is 3 times higher than the electric signal to pseudorabies virus (denoted as S1462-P7-PRV), porcine coronavirus (denoted as FCOV-P7), and porcine circovirus type 2 (denoted as 110-873S) with $10^{-3}$ dilution. Therefore, the results show that the antibody 142 has low cross-reactivity, indicating that the antibody 142 has high specificity to PRRSV.

Figure 2B:
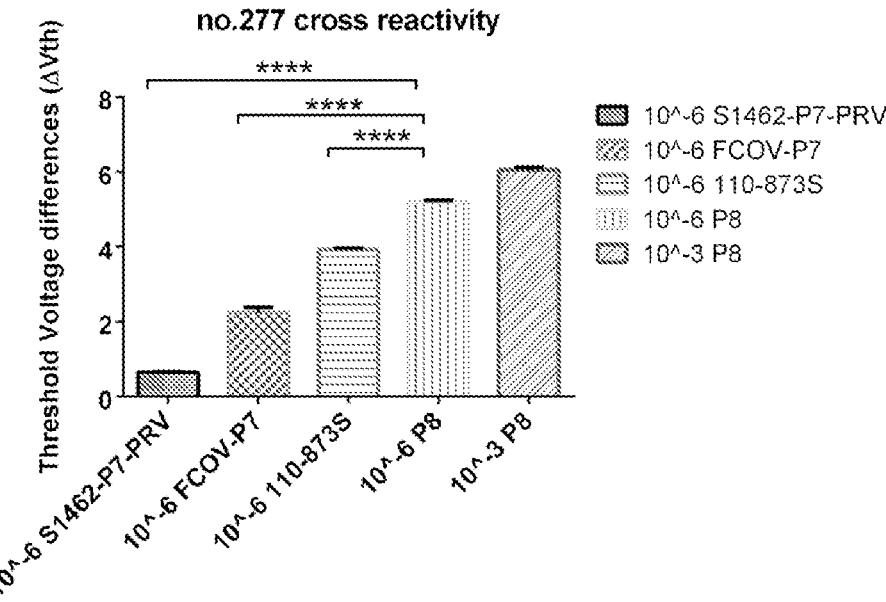
FIG. 2B illustrates the cross-reactivity of anti-PRRSV antibody 277 (denoted as no. 277) to PRRSV (denoted as 763-P8), pseudorabies virus (denoted as S1462-P7-PRV), coronavirus (denoted as FCOV-P7), or porcine circovirus type 2 (denoted as 110-873S) when being applied on Bio-FET.

The result of the cross-reactivity of the antibody 277 to PRRSV (denoted as 763-P8), pseudorabies virus (denoted as S1462-P7-PRV), porcine coronavirus (denoted as FCOV-P7), and porcine circovirus type 2 (denoted as 110-873S) is shown in FIG. 2B. Those samples are used with $10^{-6}$ and $10^{-3}$ dilution. As shown in FIG. 2B, the electric signals of the anti-PRRSV antibody 277 to PRRSV (denoted as 763-P8) with $10^{-6}$ dilution is significantly higher than the electric signals to pseudorabies virus (denoted as S1462-P7-PRV), porcine coronavirus (denoted as FCOV-P7), and porcine circovirus type 2 (denoted as 110-873S) with $10^{-6}$ dilution. Moreover, only the electric signal of the anti-PRRSV antibody 277 to PRRSV (denoted as 763-P8) with $10^{-6}$ dilution is 3 times higher than the electric signal to pseudorabies virus (denoted as S1462-P7-PRV) with $10^{-6}$ dilution. Therefore, the results show that the anti-PRRSV antibody 277 has higher cross-reactivity and would have non-specific binding to porcine coronavirus (denoted as FCOV-P7) and porcine circovirus type 2 (denoted as 110-873S), indicating that the anti-PRRSV antibody 277 has lower specificity when being applied on the Bio-FET.

As aforementioned, when being applied on the ELISA, the antibodies 142 and 277 both show high specificity and sensitivity to PRRSV. However, when being applied on the Bio-FET, the antibody 142 shows high specificity and sensitivity to PRRSV while the antibody 277 does not, which indicates that the antibody 142 could not only be applied on the ELISA, but also be a good candidate for Bio-FET field to detect PRRSV.

Application

For the application of detection PRRSV, the anti-PRRSV antibodies 142 and 277 are able to detect an animal (e.g., pig) infected with PRRSV by using assays such as Enzyme-linked immunosorbent assay (ELISA), or using Biochip devices (e.g., Bio-FET).

What is claimed is:

1. An antibody or antigen-binding fragment thereof for binding to Porcine Reproductive and Respiratory Syndrome Virus (PRRSV), the antibody or antigen-binding fragment thereof comprising:

a heavy chain variable domain comprising:

a heavy chain complementarity-determining region 1 (CDR-H1) comprising the sequence of SEQ ID NO: 1, a CDR-H2 comprising the sequence of SEQ ID NO: 2, and a CDR-H3 comprising the sequence of SEQ ID NO: 3; and a light chain variable domain comprising:

a light chain complementarity-determining region 1 (CDR-L1) comprising the sequence of SEQ ID NO: 4, a CDR-L2 comprising the sequence of Ala-Ala-Ser, and a CDR-L3 comprising the sequence of SEQ ID NO: 5.

2. The antibody or antigen-binding fragment thereof of claim 1, wherein the heavy chain variable domain further comprises the sequence of SEQ ID NO: 6.

3. The antibody or antigen-binding fragment thereof of claim 1, wherein the light chain variable domain further comprises the sequence of SEQ ID NO: 7.

4. An isolated nucleic acid encoding the antibody or antigen-binding fragment thereof of claim 1, wherein the isolated nucleic acid encoding the antibody or antigen-binding fragment thereof comprises a first fragment encoding the heavy chain variable domain and a second fragment encoding the light chain variable domain.

5. The isolated nucleic acid encoding the antibody or antigen-binding fragment thereof of claim 4, wherein the first fragment encoding the heavy chain variable domain comprises the sequence of SEQ ID NO: 8.

6. The isolated nucleic acid encoding the antibody or antigen-binding fragment thereof of claim 4, wherein the second fragment encoding the light chain variable domain comprises the sequence of SEQ ID NO: 9.

7. A vector comprising the isolated nucleic acid of claim 4.

8. A host cell comprising the vector of claim 7.

9. A method for producing an antibody or antigen-binding fragment thereof binding to Porcine Reproductive and Respiratory Syndrome Virus (PRRSV), the method comprising:

(a) culturing the host cell of claim 8 under conditions suitable for expressing the antibody or antigen-binding fragment thereof; and (b) recovering the antibody or antigen-binding fragment thereof, wherein the antibody or antigen-binding fragment thereof comprises a heavy chain variable domain and a light chain variable domain.

10. The method for producing an antibody or antigen-binding fragment thereof binding to PRRSV of claim 9, wherein the heavy chain variable domain further comprises the sequence of SEQ ID NO: 6.

11. The method for producing an antibody or antigen-binding fragment thereof binding to PRRSV of claim 9, wherein the light chain variable domain further comprises the sequence of SEQ ID NO: 7.

12. A method for detecting Porcine Reproductive and Respiratory Syndrome Virus (PRRSV), the method comprising contacting a sample with the antibody or antigen-binding fragment thereof of claim 1.

13. The method of claim 12, wherein the heavy chain variable domain further comprises the sequence of SEQ ID NO: 6.

14. The method of claim 12, wherein the light chain variable domain further comprises the sequence of SEQ ID NO: 7.

15. A biological field-effect transistor (Bio-FET), comprising:

a transistor region; and a detecting region, wherein the detecting region comprises a detecting surface that is functionalized with an antibody or antigen-binding fragment thereof binding to Porcine Reproductive and Respiratory Syndrome Virus (PRRSV), wherein the antibody or antigen-binding fragment thereof comprises:

a heavy chain variable domain comprising a heavy chain complementarity-determining region 1 (CDR-H1) comprising the sequence of SEQ ID NO: 1, a CDR-H2 comprising the sequence of SEQ ID NO: 2, and a CDR-H3 comprising the sequence of SEQ ID NO: 3; and a light chain variable domain comprising a light chain complementarity-determining region 1 (CDR-L1) comprising the sequence of SEQ ID NO: 4, a CDR-L2 comprising the sequence of Ala-Ala-Ser, and a CDR-L3 comprising the sequence of SEQ ID NO: 5.

16. The Bio-FET of claim 15, wherein the heavy chain variable domain further comprises the sequence of SEQ ID NO: 6.

17. The Bio-FET of claim 15, wherein the light chain variable domain further comprises the sequence of SEQ ID NO: 7.

18. A method for detecting Porcine Reproductive and Respiratory Syndrome Virus (PRRSV) by using a biological field-effect transistor (Bio-FET), the method comprising:

(a) contacting a sample with an antibody or antigen-binding fragment thereof immobilized on a detecting surface of the Bio-FET, wherein the antibody or antigen-binding fragment thereof comprises:

a heavy chain variable domain comprising a heavy chain complementarity-determining region 1 (CDR-H1) comprising the sequence of SEQ ID NO: 1, a CDR-H2 comprising the sequence of SEQ ID NO: 2, and a CDR-H3 comprising the sequence of SEQ ID NO: 3; and light chain variable domain comprising a CDR-L1 comprising the sequence of SEQ ID NO: 4, a CDR-L2 comprising the sequence of Ala-Ala-Ser, and a CDR-L3 comprising the sequence of SEQ ID NO: 5, wherein the antibody or antigen-binding fragment thereof binds to PRRSV; and (b) analyzing an electric signal obtained from the Bio-FET.

19. The method of claim 18, wherein the heavy chain variable domain further comprises the sequence of SEQ ID NO: 6.

20. The method of claim 18, wherein the light chain variable domain further comprises the sequence of SEQ ID NO: 7.

* * * * *

```
                        SEQUENCE LISTING

Sequence total quantity: 14
SEQ ID NO: 1              moltype = AA  length = 9
FEATURE                  Location/Qualifiers
source                   1..9
                         mol_type = protein
                         organism = synthetic construct
SEQUENCE: 1
GYSITNDYA                                                          9

SEQ ID NO: 2              moltype = AA  length = 7
FEATURE                  Location/Qualifiers
source                   1..7
                         mol_type = protein
                         organism = synthetic construct
SEQUENCE: 2
ISYSGST                                                            7

SEQ ID NO: 3              moltype = AA  length = 16
FEATURE                  Location/Qualifiers
source                   1..16
                         mol_type = protein
                         organism = synthetic construct
SEQUENCE: 3
ARSTYGNYGY YYAMDC                                                  16

SEQ ID NO: 4              moltype = AA  length = 10
FEATURE                  Location/Qualifiers
source                   1..10
                         mol_type = protein
                         organism = synthetic construct
SEQUENCE: 4
ESIEYYGTSL                                                         10

SEQ ID NO: 5              moltype = AA  length = 8
FEATURE                  Location/Qualifiers
source                   1..8
                         mol_type = protein
                         organism = synthetic construct
SEQUENCE: 5
QQSRKVPT                                                           8

SEQ ID NO: 6              moltype = AA  length = 123
FEATURE                  Location/Qualifiers
source                   1..123
                         mol_type = protein
                         organism = synthetic construct
SEQUENCE: 6
EVQRVESGPG LVKPSQSLSL TCTVTGYSIT NDYAWNWIRQ FPGNKLEWMG YISYSGSTSY  60
NPYLKSRISI TRDTSKNQFF LQLNSVPTED TATYYCARST YGNYGYYYAM DCWGQGTSVT  120
VSS                                                               123

SEQ ID NO: 7              moltype = AA  length = 111
```

-continued

```
FEATURE                Location/Qualifiers
source                 1..111
                       mol_type = protein
                       organism = synthetic construct
SEQUENCE: 7
DIVLTQSPAS LAVSLGQRAT ISCRASESIE YYGTSLMQWY QQKPGQPPKL LIYAASNVES   60
GVPARFSGSG SGTDFSLNIH PVEEDDIAMY FCQQSRKVPT FGGGTKLEIK R           111

SEQ ID NO: 8           moltype = DNA   length = 368
FEATURE                Location/Qualifiers
source                 1..368
                       mol_type = other DNA
                       organism = synthetic construct
SEQUENCE: 8
gaggtgcagc gggtggagtc gggacctggc ctggtgaaac cttctcagtc tctgtccctc   60
acctgcactg tcactggcta ctcaatcacc aatgattatg cctggaactg gatccggcag  120
tttccaggaa acaaactgga gtggatgggc tacataagct acagcggcag cactagctac  180
aacccatatc tcaaaagtcg aatctctatc actcgagaca catccaagaa ccagttcttc  240
ctgcagttga attctgtgcc tactgaggac acagccacat attactgtgc aagatccacg  300
tatggtaact acggatatta ctatgctatg gactgctggg tcaaggaac ctcagtcacc  360
gtctcctc                                                          368

SEQ ID NO: 9           moltype = DNA   length = 333
FEATURE                Location/Qualifiers
source                 1..333
                       mol_type = other DNA
                       organism = synthetic construct
SEQUENCE: 9
gacattgtgc tcacccaatc tccagcttct ttggctgtgt ctctagggca gagagccacc   60
atctcctgca gagccagtga aagtattgaa tattatggca caagtttaat gcagtggtac  120
caacagaaac caggacagcc acccaaactc ctcatctatg ctgcatccaa cgtagaatct  180
ggggtccctg ccaggtttag tggcagtggg tctgggacag acttcagcct caacatccat  240
cctgtggagg aggatgatat tgcaatgtat ttctgtcagc aaagtaggaa ggttccgacg  300
ttcggtggag gcaccaagct ggaaatcaaa cgt                               333

SEQ ID NO: 10          moltype = DNA   length = 27
FEATURE                Location/Qualifiers
source                 1..27
                       mol_type = other DNA
                       organism = synthetic construct
SEQUENCE: 10
ggctactcaa tcaccaatga ttatgcc                                       27

SEQ ID NO: 11          moltype = DNA   length = 21
FEATURE                Location/Qualifiers
source                 1..21
                       mol_type = other DNA
                       organism = synthetic construct
SEQUENCE: 11
ataagctaca gcggcagcac t                                             21

SEQ ID NO: 12          moltype = DNA   length = 48
FEATURE                Location/Qualifiers
source                 1..48
                       mol_type = other DNA
                       organism = synthetic construct
SEQUENCE: 12
gcaagatcca cgtatggtaa ctacggatat tactatgcta tggactgc               48

SEQ ID NO: 13          moltype = DNA   length = 30
FEATURE                Location/Qualifiers
source                 1..30
                       mol_type = other DNA
                       organism = synthetic construct
SEQUENCE: 13
gaaagtattg aatattatgg cacaagttta                                    30

SEQ ID NO: 14          moltype = DNA   length = 24
FEATURE                Location/Qualifiers
source                 1..24
                       mol_type = other DNA
                       organism = synthetic construct
SEQUENCE: 14
cagcaaagta ggaaggttcc gacg                                          24
```